(12) United States Patent
Pedenko et al.

(10) Patent No.: US 8,696,482 B1
(45) Date of Patent: Apr. 15, 2014

(54) THREE DIMENSIONAL GOLF SWING ANALYZER

(75) Inventors: Alex Pedenko, Chicago, IL (US); Alexander Panferov, Saint Petersburg (RU); Valery Ponomarev, Saint Petersburg (RU); Anatoly Badylin, Saint Petersburg (RU)

(73) Assignee: Swingbyte, Inc., Chicago, IL (US)

( * ) Notice: Subject to any disclaimer, the term of this patent is extended or adjusted under 35 U.S.C. 154(b) by 248 days.

(21) Appl. No.: 13/251,489

(22) Filed: Oct. 3, 2011

Related U.S. Application Data

(60) Provisional application No. 61/389,872, filed on Oct. 5, 2010, provisional application No. 61/532,743, filed on Sep. 9, 2011.

(51) Int. Cl.
*A63B 69/36* (2006.01)

(52) U.S. Cl.
USPC ............ 473/223; 473/221; 473/222; 702/150

(58) Field of Classification Search
USPC .................................. 473/221–223; 702/105
See application file for complete search history.

(56) References Cited

U.S. PATENT DOCUMENTS

| | | |
|---|---|---|
| 3,945,646 A | 3/1976 | Hammond |
| 4,150,825 A | 4/1979 | Wilson |
| 4,429,880 A | 2/1984 | Chen et al. |
| 4,695,953 A | 9/1987 | Blair et al. |
| 5,067,718 A | 11/1991 | Knox et al. |
| 5,108,105 A | 4/1992 | Shimizu |
| 5,257,084 A | 10/1993 | Marsh |
| 5,301,947 A | 4/1994 | Kim |
| 5,332,225 A | 7/1994 | Ura |
| 5,447,305 A | 9/1995 | Socci et al. |
| 5,453,758 A | 9/1995 | Sato |
| 5,478,076 A | 12/1995 | Desjardins |
| 5,516,105 A | 5/1996 | Eisenbrey et al. |
| 5,645,492 A | 7/1997 | Anderson |
| 5,692,965 A | 12/1997 | Nighan, Jr. et al. |
| 5,694,340 A | 12/1997 | Kim |
| 5,700,205 A | 12/1997 | Sanford |
| 5,704,836 A | 1/1998 | Norton et al. |
| 5,718,639 A | 2/1998 | Bouton |
| 5,741,182 A | 4/1998 | Lipps et al. |

(Continued)

FOREIGN PATENT DOCUMENTS

| | | |
|---|---|---|
| EP | 0494749 A1 | 7/1992 |
| EP | WO9745176 A1 | 12/1997 |

(Continued)

*Primary Examiner* — Corbett B Coburn
(74) *Attorney, Agent, or Firm* — Perry Hoffman

(57) ABSTRACT

An apparatus and method for golf swing analysis is described using a first microprocessor, a three-axis accelerometer capable of transmitting linear acceleration data to the first microprocessor, a three-axis gyroscope capable of transmitting angular velocity data to the first microprocessor, data processing, a radio transmitter for transmitting processed data, and a housing for holding the components, which attaches to a golf club. A three-axis magnetometer capable of transmitting directional orientation data to the first microprocessor is used to allow a user to choose a target line. Communication occurs between the apparatus and a portable device with a radio receiver, memory and a computer program that processes the data into graphical data and statistical data and displays the swing graphically after a user swings the golf club. The user will be able to analyze and try to improve his or her golf swing.

20 Claims, 18 Drawing Sheets

(56) References Cited

U.S. PATENT DOCUMENTS

| | | |
|---|---|---|
| 5,826,874 A | 10/1998 | Teitell et al. |
| 5,833,549 A | 11/1998 | Zur et al. |
| 5,860,648 A | 1/1999 | Petermeier et al. |
| 5,941,779 A | 8/1999 | Zeiner-Gundersen |
| 6,073,086 A | 6/2000 | Marinelli |
| 6,162,123 A | 12/2000 | Woolston |
| 6,375,579 B1 | 4/2002 | Hart |
| 6,441,745 B1 | 8/2002 | Gates |
| 7,021,140 B2 | 4/2006 | Perkins |
| 7,234,351 B2 | 6/2007 | Perkins |
| 7,691,004 B1 | 4/2010 | Lueders |
| 7,785,211 B2 | 8/2010 | Hackenberg |
| 7,914,289 B1 | 3/2011 | Haley |
| 7,978,081 B2 * | 7/2011 | Shears et al. ............... 340/573.1 |
| 8,257,191 B2 | 9/2012 | Stites et al. |
| 8,465,376 B2 * | 6/2013 | Bentley ...................... 473/221 |
| 2002/0077189 A1 | 6/2002 | Tuer et al. |
| 2002/0123386 A1 | 9/2002 | Perlmutter |
| 2003/0207718 A1 | 11/2003 | Perlmutter |
| 2006/0166737 A1 * | 7/2006 | Bentley ........................ 463/30 |
| 2006/0184336 A1 * | 8/2006 | Kolen ........................... 702/150 |
| 2007/0206837 A1 | 9/2007 | Kirby |
| 2010/0049468 A1 | 2/2010 | Papadourakis |
| 2010/0255922 A1 | 10/2010 | Lueders |
| 2012/0295726 A1 * | 11/2012 | Cherbini ..................... 473/222 |
| 2013/0267335 A1 * | 10/2013 | Boyd et al. .................. 473/222 |

FOREIGN PATENT DOCUMENTS

| | | |
|---|---|---|
| GB | 2318982 A | 5/1998 |
| SU | 814373 | 3/1981 |
| WO | WO0069528 A1 | 11/2000 |
| WO | WO0235184 A3 | 5/2002 |

* cited by examiner

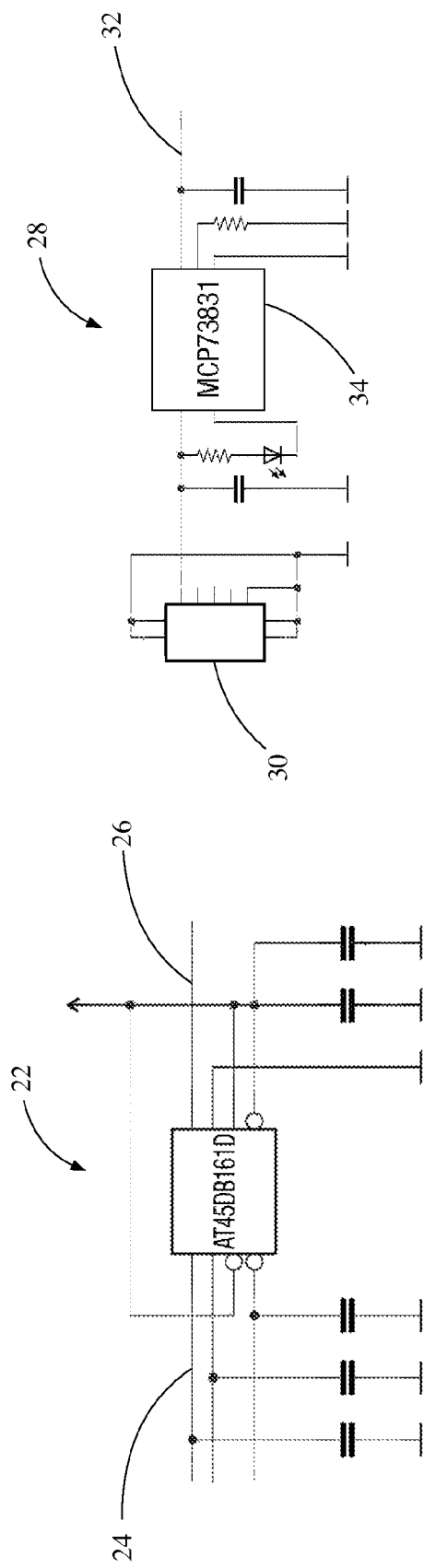

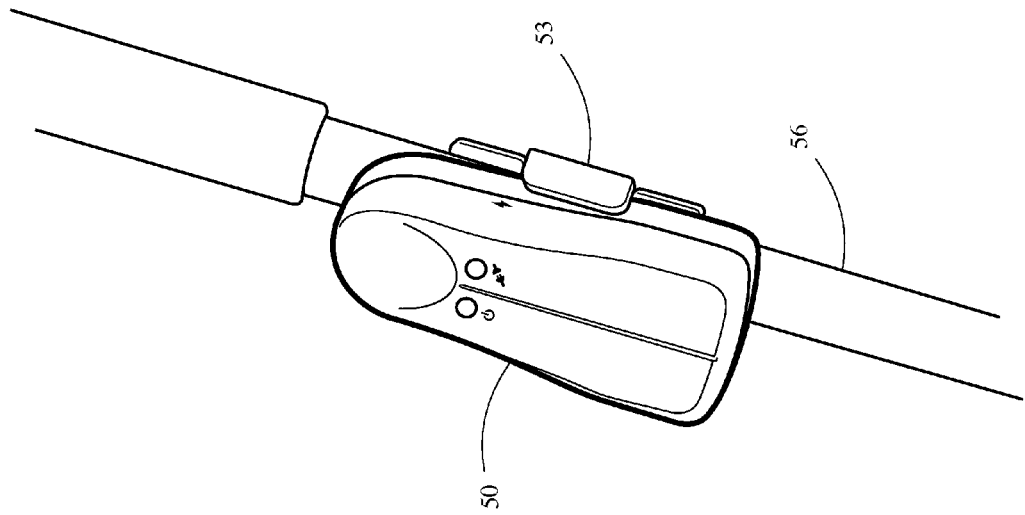

THREE DIMENSIONAL GOLF SWING ANALYZER

PRIORITY REFERENCE

This application claims priority from Provisional Patent Applications, Nos. 61/389,872 filed on Oct. 5, 2010, and 61/532,743, filed on Sep. 9, 2011, which are expressly incorporated herein by reference.

FIELD OF THE INVENTION

The present invention relates generally to analyzing linear and angular movement using a graphical animation of such movement and statistics related to such movement, and more particularly to analyzing a golf swing, for example, by attaching an apparatus to a golf club wherein the apparatus communicates with a mobile device such as a smart phone or a tablet computer and graphically shows the golf swing along with relevant statistics to help a golfer analyze and improve his or her golf swing.

BACKGROUND OF THE INVENTION

Over the past several years, the popularity of golf has soared, leading to a great number of inventions that allow a player to get enjoyment by playing a simulated game or to practice by using a machine to analyze a player's golf swing.

Particularly relevant to game simulation are inventions in the prior art using gesture recognition to allow a player to make realistic movements that are mimicked on a video display. For example, a player playing a simulated golf game can use a real or mock golf club to make the movements of an actual golf swing and see the mimicked swing on a video display followed by the graphical representation of a golf ball flying off a graphical tee, hopefully towards a graphical hole. U.S. Pat. No. 5,453,758, issued to Sato, for "Input Apparatus" "outputs as operator information the position specifying information obtained by detecting input apparatus's physical displacement, movement velocity, or acceleration to generate a predetermined command signal corresponding to movements of a human being for example". Sato further discloses using an oscillation gyroscope to sense angular velocity and a temperature sensor to correct errors in movement related data caused by changing temperature conditions. U.S. Pat. No. 5,516,105, issued to Eisenbrey, et al., for "Acceleration Activated Joystick" discloses a "video game user interface device that allows the user to play standard video games using realistic arm, leg and body movements which relate to the various activities portrayed in the video game being played. The device is sensitive to acceleration and outputs a signal to the video game controller when an acceleration is detected." U.S. Pat. No. 5,704,836, issued to Norton, et al., for "Motion-Based Command Generation Technology" discloses a command system that "optically monitors the movement of a subject and provides command signals to a computer system to control a graphic of a graphical user interface displayed on a monitor such as an animated character in a video game." Norton accomplishes this by using an "optical detector unit which continuously scans a subject frame in which a subject is positioned" and comparisons of scans of sub-regions in the frame to determine if the subject has moved. Once movement is detected, the graphical representation on a video screen can simulate the movement. U.S. Pat. No. 5,718,639, issued to Bouton, for "Opto-Electric Golf Club Swing Sensing System Having Vertically Offset Sensors" discloses a "video golf swing sensing system responsive to a user swinging a golf club" that "provides inputs to a video golf game operating on a personal computer having a monitor, a microprocessor, and a serial port." Bouton uses a sensing system comprising linear arrays of LEDs and photodetectors "for detecting a club head parameter by sensing light reflected off the club head." These gesture recognition apparatuses and methods in the prior art use sophisticated mapping schemes to let a user participate in simulated activities using motions that would be used in the real activity.

Particularly relevant to golf swing analysis are inventions in the prior art that measure certain characteristics of a golf swing such as club speed and position. U.S. Pat. No. 5,108,105, issued to Shimizu, for "Golf Practice Device" discloses a "golf practice device comprising a mat with at least two sensors arranged therein in the direction of a swing orbit of a head of a golf club. A swing time substantially from a start of a back swing to a point of an impact with a golf ball is calculated in response to signals output by the sensors, and the result is indicated so that a golfer can observe same and thus achieve a stable swing." U.S. Pat. No. 5,257,084, issued to Marsh, for "Golf Swing Measurement System" discloses "A technique for measuring golf swing tempo or clubhead speed for a golfer swinging a golf club through a tee area. Two parallel infrared (IR) transmitters transmit respective IR beams along predetermined lines toward the tee area. Respective IR sensors receive respective IR beams reflected from a reflector mounted to the shaft of the golf club, near the clubhead. Each IR sensors provides a respective output signal indicative of the passage of the golf club through a corresponding IR beam. Predetermined sequences of output signals from the IR sensors are detected and the differences in time between various output signals are measured to provide tempo and clubhead speed values for display on a LCD screen. The speed values can be compensated values as obtained from look-up tables." U.S. Pat. No. 5,692,965, issued to Nighan, et al., for "Golf Swing Training Device With Laser" discloses an apparatus that uses at least one laser device that provides a feedback signal to the golfer that is indicative of a position and a motion of the head during the top of a backswing of the golf club by the golfer." The laser device may also be used to project a beam that provides visual feedback to the user, such as by showing a path on the ground or the motion and position of the golf club head. U.S. Pat. No. 6,375,579, issued to Hart, for "Golf Swing Analysis System And Method" discloses a laser based system that uses a monochromatic laser projector to generate a series of light planes in space near the impact zone where the golf club impacts the golf ball and a laser-based attachment for the golf club. This system and method attempts to analyze an entire golf swing by measuring certain characteristics of a golf swing as it passes through the impact zone. U.S. Pat. No. 7,785,211, issued to Hackenberg, for "Golf Swing Trainer Having Balanced Center Of Mass" discloses a "golf swing trainer providing a resiliently flexible shaft having a first shaft end coupled to a swing element and a second shaft end coupled to a grip having a tapered external surface gripably received by the hands."

The prior art is deficient because it does not provide an apparatus and method of providing an attachment to a golf club that detects and measures the movement of the golf club through an entire swing, that displays the entire swing movement of the golf club on a graphical display along with relevant statistics, and that provides coaching using theoretical and historical data with graphical and verbal feedback. The gesture recognition techniques described above are deficient because they are merely used as input for games and simulations and are not used to record and analyze all major aspects of a full golf swing and to provide feedback and coaching to a user so that user may improve his or her golf game. The golf swing analysis techniques described above are deficient because they attempt to analyze entire swing using only a small portion of the swing and a limited number of statistics such as club speed or they do not use a real golf club. Additionally, many inventions in the prior art require a fair amount of equipment, making them costly.

Accordingly, it would be desirable to provide a lightweight attachment to a golfer's actual golf club that detects and measures the movement of a full golf swing, that analyzes the entire golf swing, that provides comprehensive statistics for every point of an entire swing, that displays the movement of the entire swing on a graphical display with the comprehensive statistics, and that coaches the golfer on how to improve the swing using theoretical and historical data. This can be accomplished by attaching an apparatus of negligible weight to the shaft or top of a golf club where the apparatus comprises a 3-axis accelerometer, a 3-axis gyroscope, computer memory, a microprocessor, a transmitter, and a battery such that is communicates with a computer application running on a mobile device such as a smart phone, tablet computer, or a laptop computer. To compensate for differences in the angles that individual golfers address the ball, a 3-axis magnetometer can be used to select the target line on which a golfer wishes to aim. The inventions discussed in connection with the described embodiment address these and other deficiencies of the prior art.

The features and advantages of the present inventions will be explained in or apparent from the following description of the preferred embodiment considered together with the accompanying drawings.

SUMMARY OF THE INVENTION

The present inventions address the deficiencies of the prior art of golf swing analysis and coaching. Particularly, a small attachment of negligible weight that is securable to the shaft of a golf club, or mountable inside a hollow golf club, is used to communicate to an application running on a mobile device such as a smart phone, a tablet computer, or a laptop computer. The attachment uses a transmitter to send processed linear and angular movement data that defines a golf swing to a receiver on the mobile device. A computer application running on the mobile device receives the processed data, processes the data further and displays a graphical representation of the entire swing with comprehensive statistics for every point of the swing. The processed data is stored and later used along with theoretical data to coach a golfer on his or her swing. Thus, unlike the prior art, a golfer can fully analyze a golf club swing at every point of the swing and make proper adjustments at any point in the swing to improve the swing.

More particularly, the present inventions include a three-axis accelerometer capable of producing and transmitting linear acceleration data, a three-axis gyroscope capable of producing and transmitting angular velocity data, a first microprocessor that receives data from the accelerometer and the gyroscope and processes the data, a first computer memory wherein the microprocessor stores the processed data, and a radio transmitter for transmitting the processed data from the first computer memory. The inventions are powered by a battery or other suitable power source. A housing is used to hold the accelerometer, the gyroscope, the microprocessor, the computer memory, the radio transmitter, and the battery. MEMS technology may be used for the accelerometer and the gyroscope. Other suitable motion detectors may be used that provide the same functionalities as the accelerometer and the gyroscope. Flash memory may be used as the computer memory. To compensate for differences in the angles that individual golfers address the ball, a 3-axis magnetometer may be used to select the target line on which a golfer wishes to aim. Thus, a golfer may account for that golfer's natural slice or hook.

The inventions further have a portable device, such as a smart phone, a tablet computer, or a laptop computer, that includes a radio receiver, a second computer memory for storing data received by the radio receiver, a third computer memory for storing a computer program that processes the data in the second computer memory, a second microprocessor for controlling the computer program and for processing the data received by the radio receiver into graphical data and statistical data, a fourth computer memory for receiving graphical data and statistical data from the second microprocessor, and a graphics display.

The housing, which is of negligible weight so that it does not affect a golf swing, attaches to a the shaft of the golf club below the grip or at the top of the grip, and, when a user swings the golf club, the accelerometer communicates linear acceleration data defining the linear movements of the golf club to the first microprocessor and the gyroscope communicates angular velocity data defining the angular movements of the golf club to the first microprocessor. The first microprocessor processes the linear acceleration data and the angular velocity data, stores the processed data in the first computer memory, and uses the radio transmitter to transmit the processed data to the radio receiver on the portable device. The radio receiver stores the processed data in the second computer memory. The computer program stored in the third computer memory is controlled by the second microprocessor to store graphical data and statistical data in the fourth computer memory and to display the graphical data and the statistical data on the graphics display as an image of the movement of the golf club along with related statistics. Using the display and the statistics, the user will be able to analyze and try to improve his or her golf swing. The housing may also be the hollow shaft of a golf club.

In described embodiments of the present inventions, the graphics display shows an interactive three-dimensional animation of the swing wherein the animation can be played as slowly or as quickly as a user desires, the animation can be played from any angle, and the animation can be played at any magnification. Additionally, the graphics display can show the position, orientation, and speed of the golf club at any point throughout the swing. Also, the graphics display shows metrics that allow one to analyze a golf swing such as club head speed at any point in the swing, club and ball path, tempo, top of backswing, angle of attack, relevant planes, and relevant angles. Embodiments of the inventions provide further analysis wherein the computer program compares the position of the club when the user aims with the position of the club on impact and calculates the difference in loft, lie and club face angles between the two positions to allow the user to compare what the user meant to do with what actually happened. Embodiments of the inventions also provide verbal instructions and analysis of the golf club swing.

The present inventions may also include a user input device for inputting a user's biometric data and a fifth computer memory for storing user biometric data wherein the second microprocessor controls the computer program to factor the user biometric data into the processed data.

The described inventions may also be used with a website wherein the second microprocessor controls the computer program in the third computer memory to upload the graphical data and the statistical data from the fourth computer memory to the website for personal review and for sharing with other users. Consequently, the website provides coaching based on the processed data. The website also allows a user to compare multiple swings at once using that user's history of uploaded swings, allows a user to enter biometric data and to view baseline swings for that user's body type, and allows a user to see professional and theoretical swings, which allows a user to see trends over time and get objective progress data.

BRIEF DESCRIPTION OF THE DRAWINGS

The inventions will now be more particularly described by way of example with reference to the accompanying drawings. Novel features believed characteristic of the inventions are set forth in the claims. The inventions themselves, as well as the preferred mode of use, further objectives, and advantages thereof, are best understood by reference to the following detailed description of the embodiment in conjunction with the accompanying drawings, in which:

FIG. 1C shows a schematic of flash memory.

FIG. 1D shows a schematic of a battery charger.

FIG. 2A shows a front perspective view of the housing attached to a golf club.

DETAILED DESCRIPTION OF THE EMBODIMENTS

Figure 1B:
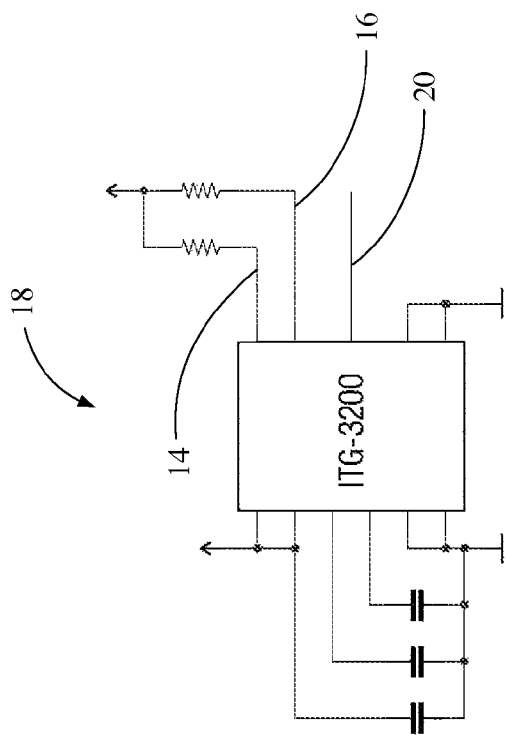
FIG. 1B shows a schematic of a gyroscope.

The described embodiment is a three-dimensional golf swing analyzer for use with an application on a smart phone, a tablet computer, a laptop computer, or other similar mobile device. The device works as an Inertial Measurement Unit (IMU) attached to the shaft of a golf club to record and transmit the accelerations undergone by the club. It captures and analyzes golf swing data using a compact and lightweight sensor that attaches to any golf club either below the grip or on the cap or is integrated into the shaft. After hitting a shot or swinging the club, players and instructors can view an interactive, three-dimensional animation of the swing, along with key metrics, such as club head speed, path, plane, and various angles at impact. The user is able to see the key metrics for any point in the swing. The user can also play back the swing at any speed, from any angle, and at any magnification. Since the described embodiment is not based on video capture, but rather recording the actual position and orientation of the golf club at $\frac{1}{1000}^{th}$ of a second intervals, there are virtually no limits on the granularity of the playback. By comparing the position of the club when aiming with the position of the club at impact, the application calculates the difference in loft, lie and club face angles between the two positions, allowing the user to compare what s/he meant to do to what actually happened. Additionally, the application computes club head speed at impact (and at all points in between), tempo, top of backswing, angle of attack, club head path, and other vital characteristics. The application further provides verbal instruction and suggestions to fix common defects in a swing, such as taking the club too far back and an over-the-top swing.

The data captured may also be automatically uploaded to a website where users can access and review their historical information or share it with an instructor. The website provides additional analytics by offering advanced comparison features, allowing the user to compare multiple swings at once, including his/her own history, and baseline swings for his/her body type, as well as professional and theoretical swings. This allows the user to see trends over time, and get objective data about their progress as a golfer. This also builds the foundation for an objective instructor ranking system. The website also provides users a way to send their swing data to a third party for review. This can be used for a golfer who travels to a different part of the country for the season but who still wants to receive instruction from their teacher back home.

The following definitions will be used herein:

¼ way—the point in the backswing when the club is parallel to the ground for the first time Half-way—the point in the backswing when the projection of the club onto the earth's y-z plane is perpendicular to the horizon for the first time ¾ way—the point in the downswing when the club is parallel to the ground for the first time tobs (Top-of-backswing)—The point in the swing where the club reverses direction.

Speedpoint—The point in the swing where the club attains maximum speed

Plane angle—The angle computed at any time by taking the club's Y vector in terms of the earth's coordinate system, at the current point in the swing, and the one immediately past it. The cross product of the two vectors is taken, which produces a vector orthogonal to both of them, and the normal vector of the plane defined by the two initial vectors. The plane angle is then the angle between the earth's x-z plane and the newly computed plane.

Club face to plane angle—The club's plane is computed at address. The club face to plane angle is the angle between the x-vector of the club and this initial plane.

Club face to horizon angle—This club face to horizon angle is the angle between the x-vector of the club and the x-z plane.

The following definitions are some parameters that may be derived from the output of the apparatus:

Swing tempo/Club head speed at all points throughout the swing

Point of release—the point of the swing when the wrist angle is released during the downswing Swing plane—determine the swing plane based on address, and show deviation from it Club face/loft/lie angles—the difference in angles between address and impact.

Angle of attack—the angle of attack in the milliseconds preceding the impact

Launch direction & speed—the initial speed and direction of travel for the ball based on the impact data and the club used Torque—the amount of torque generated by the swing at all points throughout the swing Ball spin Ball flight path Ball flight distance The following data are observed from usage and may be used in analysis:

Location of use (via GPS in the user's phone)

Frequency of use

The following parameters are user defined and entered using the application on the mobile device:

Club used

Club deflection—Using the club information provided by the user and the observed torque, the application can calculate how much the club shaft will deflect.

User demographics such as age, sex, body type, handicap, frequency of play, etc.

Figure 1A:
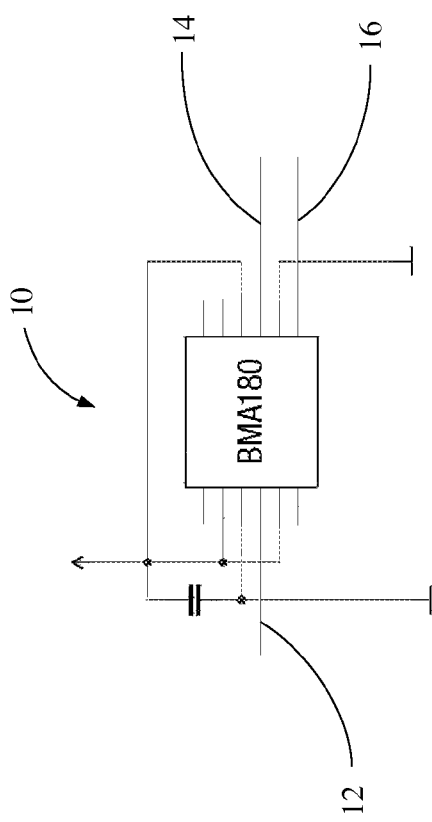
FIG. 1A shows a schematic of an accelerometer.

FIG. 1A shows a schematic of an accelerometer 10. In the described embodiment, the Bosch™ BMA180 three-axis MEMS accelerometer 10 is used, although other accelerometers may be used. In the schematic shown in FIG. 1A, the data coming from the accelerometer 10 is controlled by a linear acceleration interrupt output 12, labeled INT1, which causes the linear acceleration related data to be output on the serial data in/out line 14 to a microcontroller (described below). The accelerometer 10 is synchronized with the microcontroller using a serial clock 16.

FIG. 1B shows a schematic of a gyroscope 18. In the described embodiment, the Invensense™ ITG3200 three-axis MEMS gyroscope 18 is used, although other gyroscopes may be used. In the schematic shown in FIG. 1B, the data coming from the gyroscope 18 is controlled by an angular velocity interrupt output 20, labeled INT2, which causes the angular velocity related data to be output on the serial data in/out line 14 to a microcontroller (described below). The accelerometer 10 is synchronized with the microcontroller using a serial clock 16. Note that the accelerometer 10 and the gyroscope 18 operate with a shared serial data bus and are multiplexed using the two interrupts.

FIG. 1C shows a schematic of flash memory 22 that is used to store the data processed by the microcontroller. In the described embodiment, the Atmel™ AT45 DB161D is used, although other memory may be used. In the schematic shown in FIG. 1C, processed data from the microcontroller comes in on the flash data input line 24 and, later, the data is output on the flash data output line 26 for transmission using a transmitter.

FIG. 1D shows a schematic of the battery charger 28 that connects to a USB port 30 of the mobile device, which may be a smart phone, a tablet computer, a laptop computer, or any other similar device. The USB port 30 is used only to provide charging power to the device. FIG. 1D shows that the described embodiment uses a Microchip MCP73831 charge management controller 34, but other charge management controllers may be used. The power circuitry of the device provides charge on the battery charger line 32 to a battery 36 as shown in FIG. 1E.

Figure 1E:
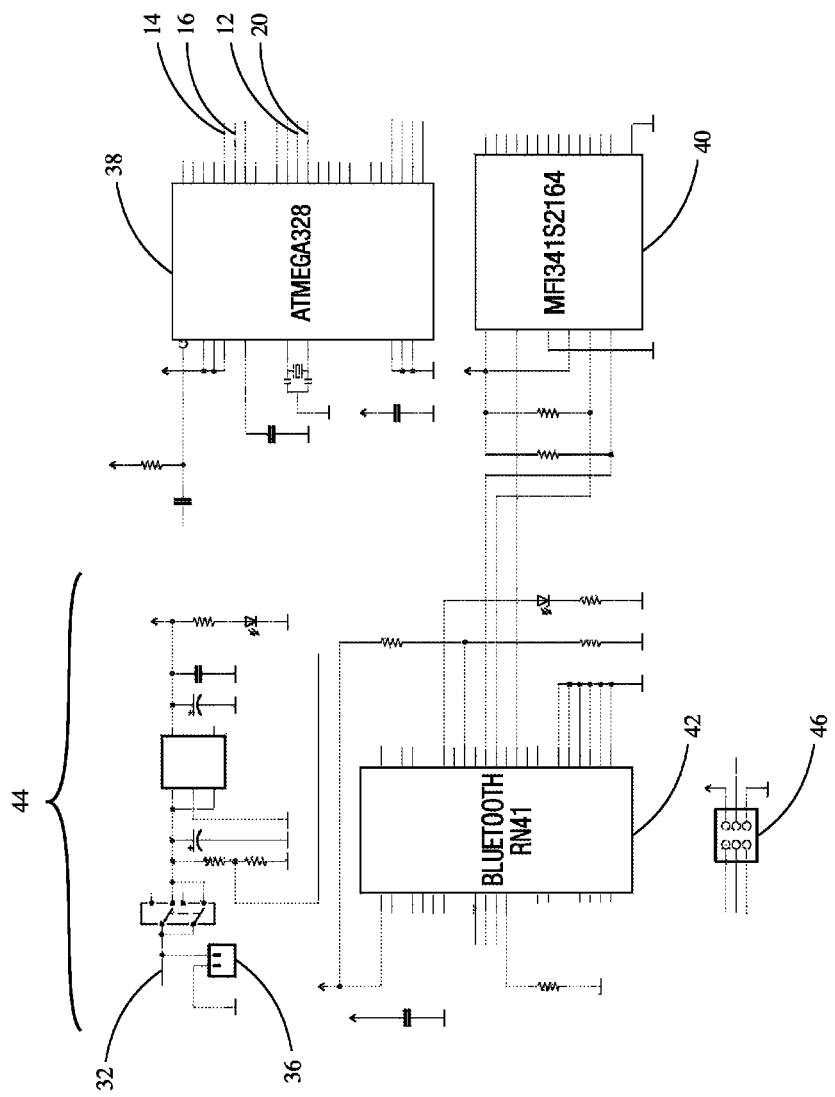
FIG. 1E shows a schematic of a microcontroller, co-processor, radio transmitter, and power control.

FIG. 1E shows a schematic of a microcontroller 38, co-processor 40, radio transmitter 42, and power control 44. This figure shows the layout of the various components utilized and reveals how the serial data in/out line 14 and the serial clock 16 come into the microcontroller 38 on the shared bus. In the described embodiment, the microcontroller 38 is an Atmel ATmega328, although other microcontrollers may be used. This figure also reveals how the linear acceleration interrupt output 12 and the angular velocity interrupt output 20 are connected to the microcontroller 38. Further shown in FIG. 1E is how a co-processor 40 is used to assist the transmission of processed data using a radio transmitter 42. In the described embodiment, the co-processor 40 is an Apple™ MFI341S2164, although other co-processors may be used. Under the control of the microcontroller 38, the co-processor 40 communicates to a radio transmitter 42 to transmit data to a mobile device. In the described embodiment, the radio transmitter 42 is a Bluetooth RN41, although other radio transmitters may be used. Although the function of the radio transmitter 42 is to transmit processed golf swing data, the radio transmitter 42 should be a device that may also be used as a receiver to allow remote updating of the firmware within the device. Lastly, FIG. 1E shows the USB connector 46 used to connect to a power source for charging the battery 36.

Figure 1F:
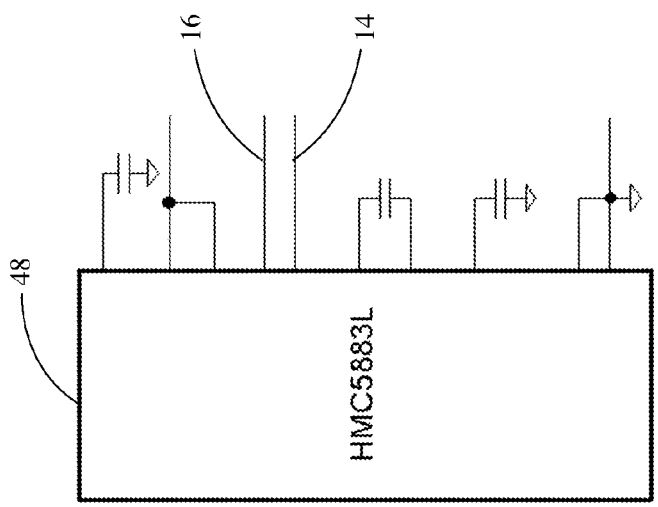
FIG. 1F shows a schematic of a magnetometer.

FIG. 1F shows a schematic of a magnetometer 48. In the described embodiment, the Honeywell™ HMC5883L digital three-axis magnetometer 48 is used, although other magnetometers may be used. FIG. 1F shows the serial data in/out line 14 and the serial clock 16 that are part of the shared serial bus. The magnetometer is used to let a user set a target line for the golf swing. This is important because each golfer displays variation in how that golfer addresses the ball and because each golfer has a different degree of natural slice or hook, including no slice or hook at all. Thus, if a golfer can choose a target line, then the actual shot can be compared to the target line for analysis and criticism. Without the target line, there is no accounting for the natural variations in how golfers address the ball. To activate this function with the magnetometer 48, a golfer starts by horizontally pointing the club, with the head down, along the desired target line, and then rotates the head of the club 180 degrees so that the club head points upward. Then, the target line will be established as the line in the direction that golf club shaft is pointing.

Figure 2B:
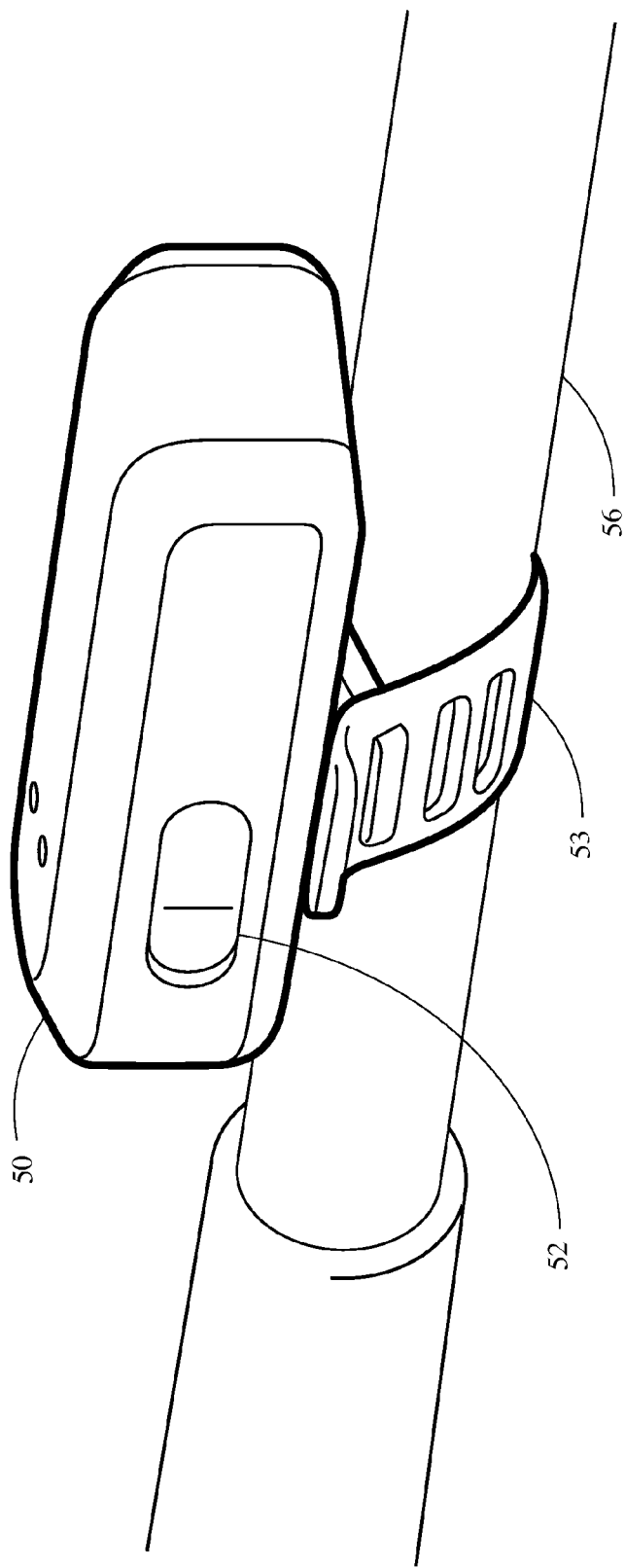
FIG. 2B shows a side perspective view of the housing attached to a golf club.
Figure 2C:
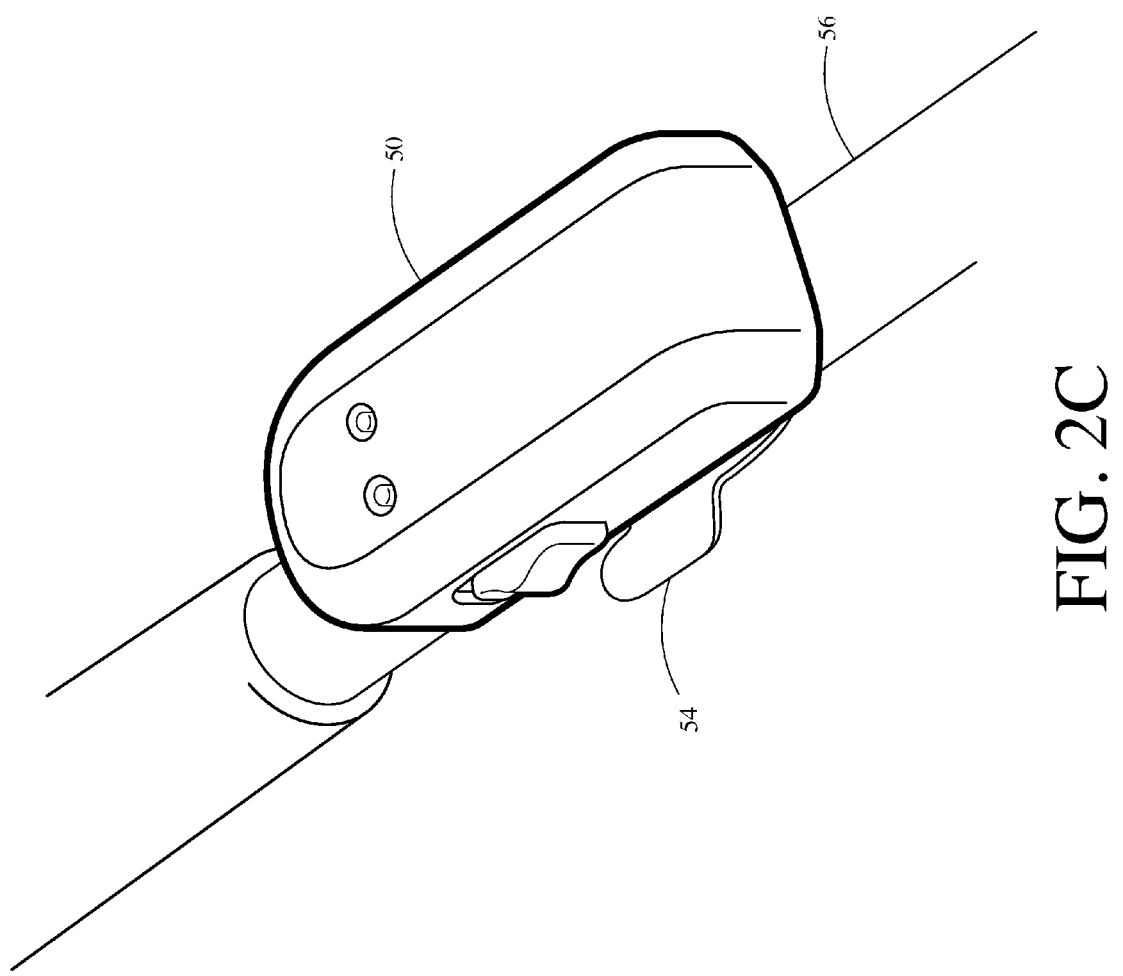
FIG. 2C shows an overhead, angled view of the housing and the strap fastener used.

FIG. 2A shows a front perspective view of the housing 50 attached to a golf club 56. This figure shows one variation on how the housing 50 may be attached to the golf club 56 using a strap 53 around the shaft of the golf club 56. FIG. 2B shows a side perspective view of the housing 50 attached to a golf club 56. Notable on this figure is the on/off switch 52, which is in close proximity to a golfer's hand and easily toggled. FIG. 2C shows an overhead, angled view of the housing 50 and the strap fastener 54 used.

Figure 3A:
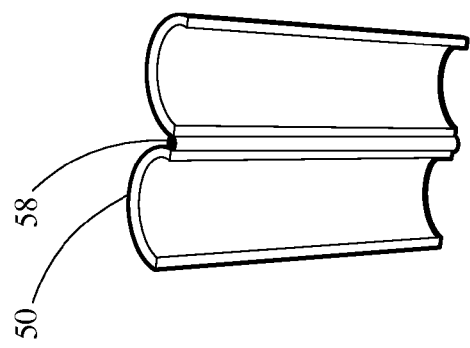
FIG. 3A shows a hinge and clasp clamp design for attaching the housing to a golf club.
Figure 3B:
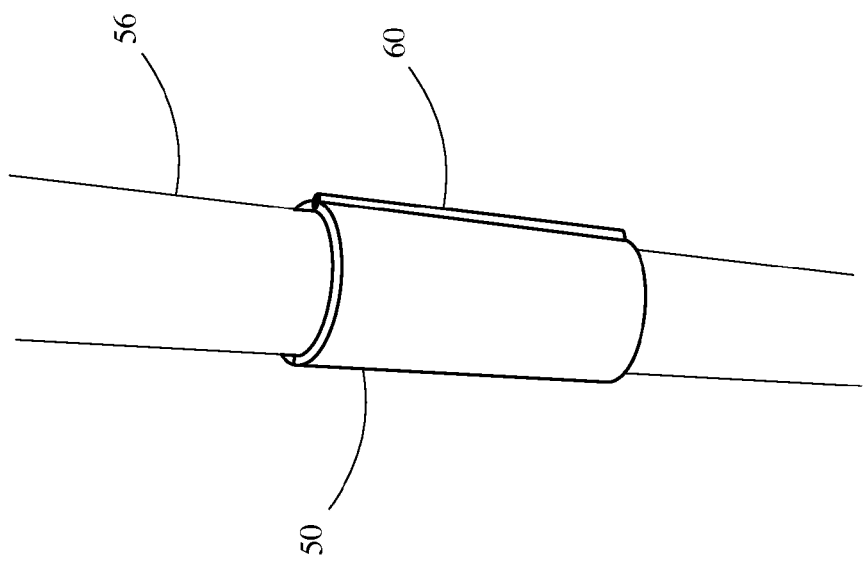
FIG. 3B shows the hinge and clasp clamp housing attached to a golf club.
Figure 4:
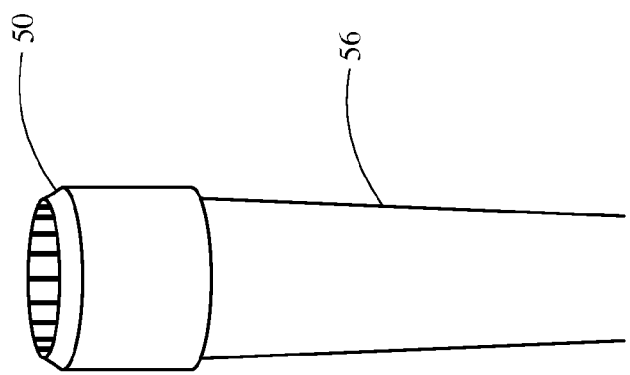
FIG. 4 shows a cap design for attaching the housing to a golf club.
Figure 5A:
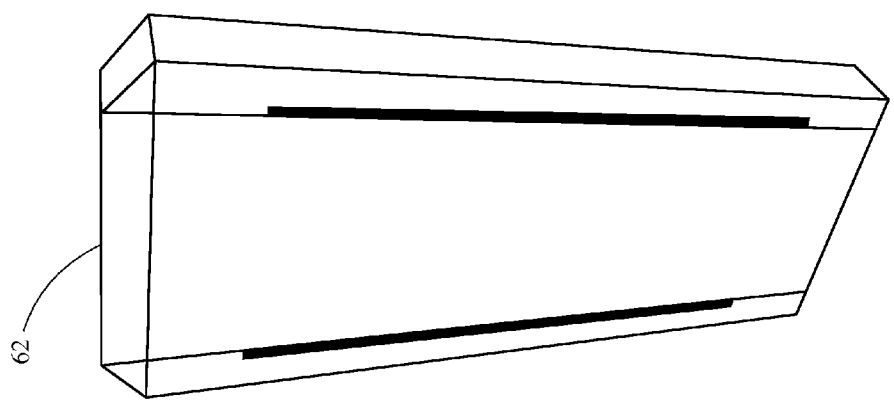
FIG. 5A shows an integrated housing for attaching around a golf club shaft.
Figure 5B:
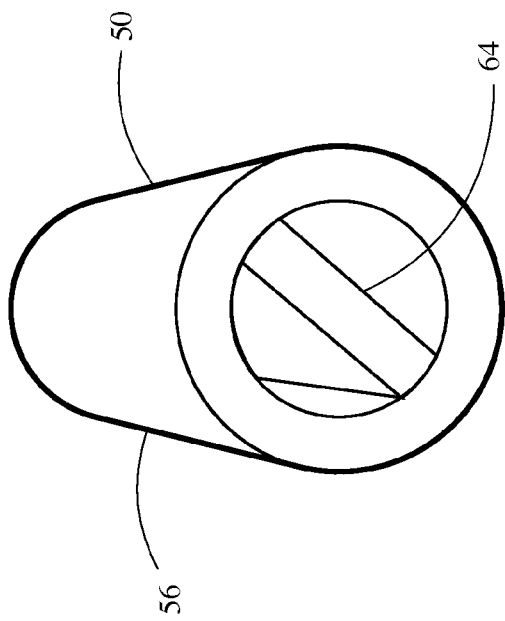
FIG. 5B shows how the a hollow club shaft may be used as the housing for holding individual components.

FIG. 3A shows a hinge 58 and clasp clamp design for attaching the housing 50 to a golf club 56. The housing 50 is such that its body rotates around the hinge 58 to wrap around a golf club 56. FIG. 3B shows the hinge 58 and clasp clamp 60 housing 50 attached to a golf club 56. This design is made to attach to the golf club 56 below the grip so that it does not interfere with the golfer's swing. FIG. 4 shows a cap design for attaching the housing 50 to a golf club 56. In this configuration, the device may be placed inside a cap fitting housing 50 at the top of the club grip. As in the housing 50 that attaches below the grip, the device is placed to not impede the golfer's swing. FIG. 5A shows an integrated housing 62 for attaching around a golf club 56 shaft. In this configuration, the individual components of the device may be placed within a specially made grip around the club 56 shaft. FIG. 5B shows how the a hollow club 56 shaft may be used as the housing 50 for holding individual components 64.

Figure 6:
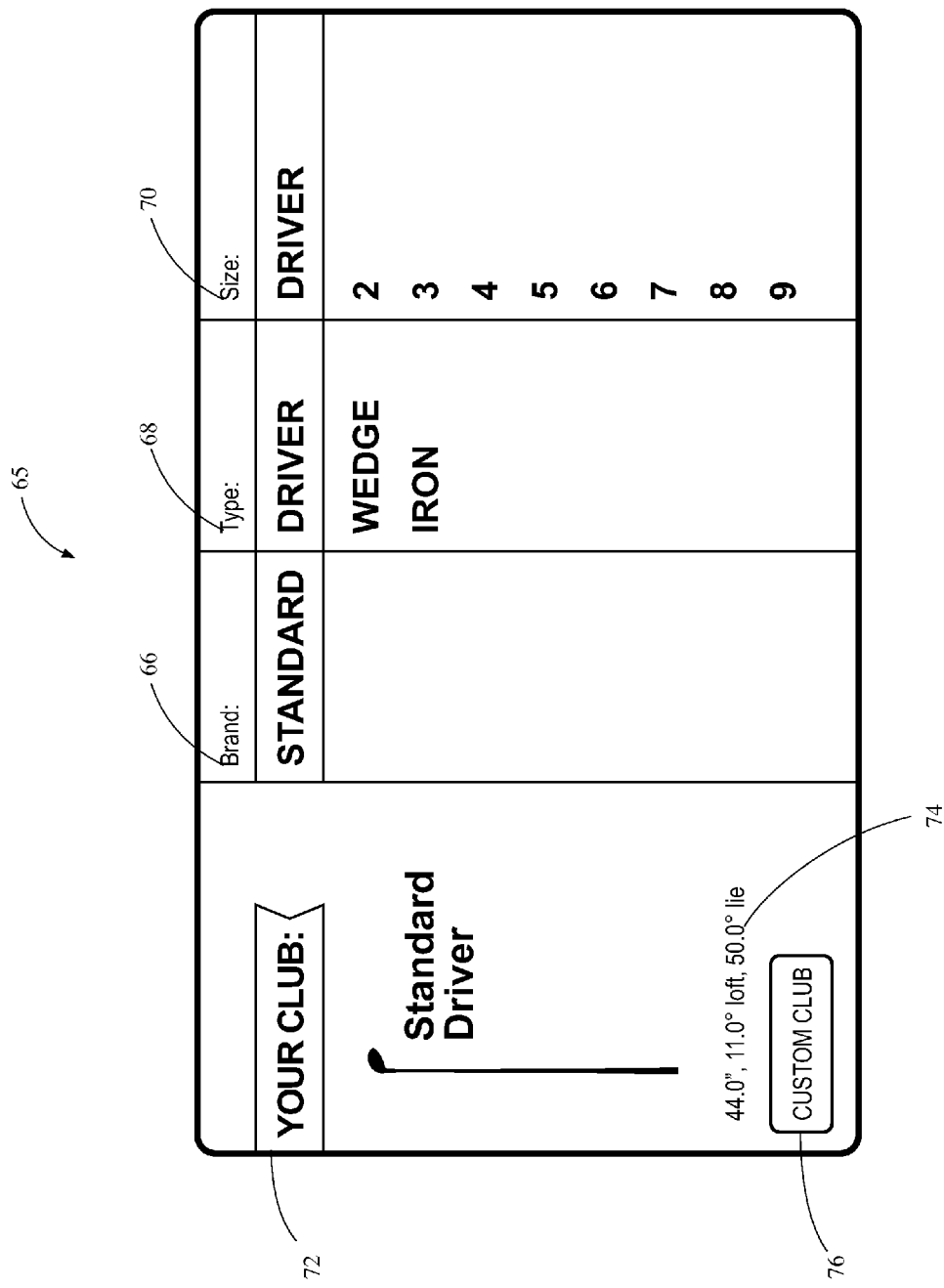
FIG. 6 shows the club selection screen for the application running on a mobile device.

FIG. 6 shows the club selection screen 65 for the application running on a mobile device. On the screen, the club brand 66 is shown and may be a standard club or a custom club. The club type 68 is labeled as a driver, a wedge, or an iron. The club size 70 will be "DRIVER" for a driver, "2" for a pitching wedge, and "3" and above for irons. A user's chosen club 72 appears on the left side of the screen. In the instance shown in FIG. 6, the user has chosen a standard driver. The club information 74, or characteristics of a standard driver, is shown towards the bottom left corner of the screen. The club information 74 is adjusted based on a user's biometrics, such as height and distance from wrist to ground. In this instance, the club is forty-four inches, with an eleven degree loft and a fifty degree lie. To use a customized club, the user may select the customization button 76. Then, the user may adjust characteristics of the club, such as length, loft, and lie.

Figure 7A:
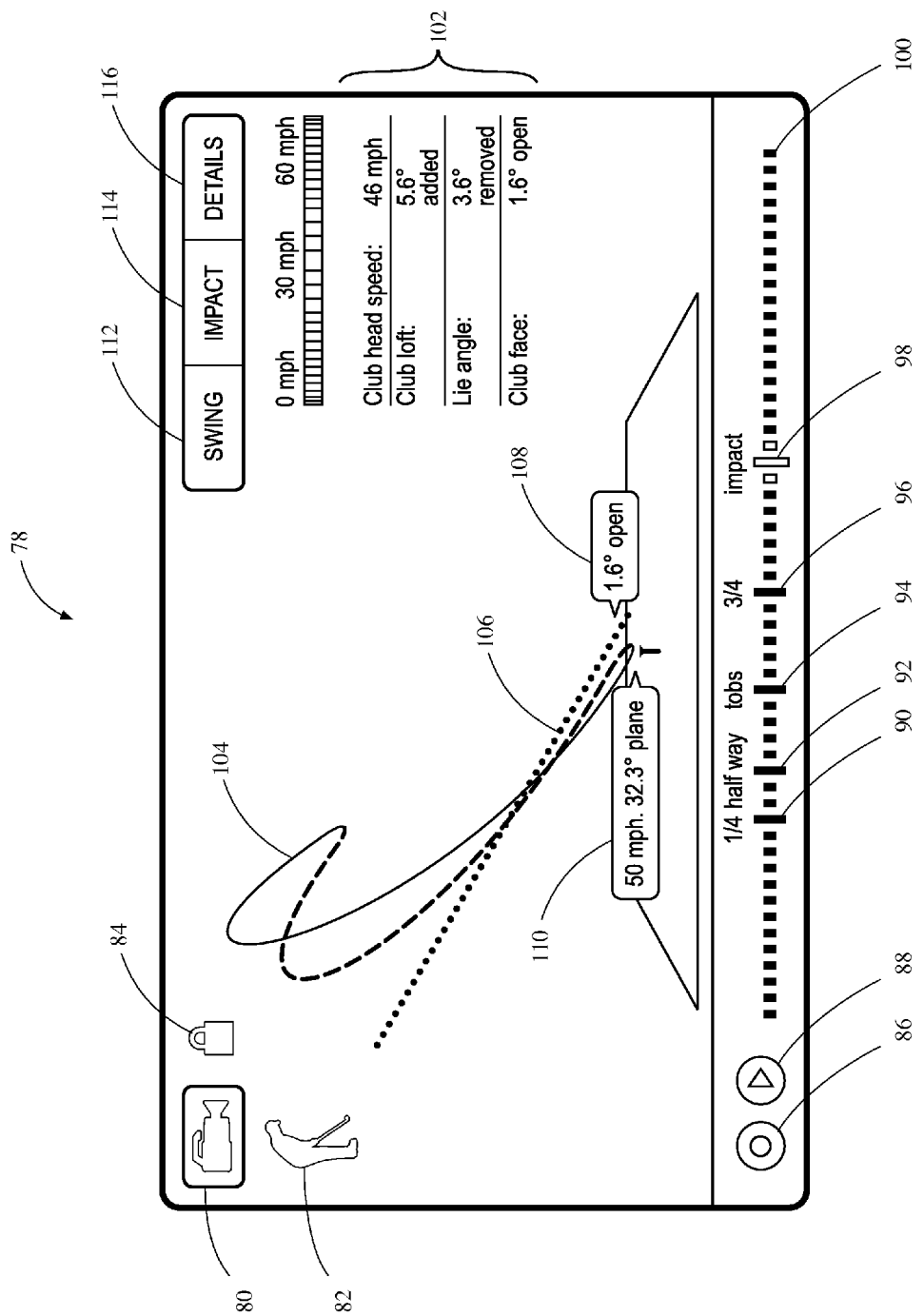
FIG. 7A shows a swing display screen for the application running on a mobile device with the outline of a full swing and summary data.

FIG. 7A shows a swing display screen 78 for the application running on a mobile device with the outline of a full swing and summary data. In general, the interface shown may be controlled with touch screen technology, using a mouse, or using some other input method. The view selector 80 is used to select one of three views, down-the-line, face on, and overhead. The current view of these three is shown by the current view indicator 82. When the locked view indicator 84 is selected, the user may change the view as if rotating a camera. To turn swing recording on and off, the user may select the recording on/off button 86. This controls whether or not the application will accept signals from the device attached to the golf club. If recording is on, then the user may swing a golf club with the device attached to the golf club and select the animation playback button 88 to see an outline of the club trajectory 104 of the swing. Along the bottom of the swing display screen 78, is the club-in-swing position bar 100, which displays the location of the club at all times, including when it crosses important points, such as the ¼ way marker 90, the half-way marker 92, the TOBS marker 94, the ¾ way marker 96, and the impact marker 98. For the screen shown in FIG. 7A, the impact marker 98 is lit to show that the club trajectory 104 at impact and related statistics are shown. After impact a club-at-impact snapshot 102 is shown that shows the club speed, the club loft, the lie angle, and how much the club face is open or closed. The club trajectory 104 is shown in the center of the screen and is color-coded by trajectory speed. The club trajectory 104 is shown in conjunction with the club initial orientation 106, the club head orientation 108 at impact, and the club at impact information 110, such as club speed and club plane, so that a user may analyze the quality of the swing. The swing display screen 78 in FIG. 7A further shows that the swing display screen was selected with the swing detail button 112. For impact detail in the form of graphics and statistics, the user may select the impact detail button 114, and to see further details, the user may select the parameter detail button 116 and see further statistics, such as the speedpoint, plane angle, club face to plane angle, club face to horizon angle, among other parameters defined above.

In order to zoom and shrink so that the user may see the club trajectory 104 and other statistics at any magnification, the user may "pinch" or "pan" the screen if it is a touch screen. The user may also increase or decrease the playback speed by moving his or her hand along the club-in-swing position bar 100 on the touch screen at whatever speed the user desires. The club-in-swing position bar 100, or progress bar, also functions as a scroll bar. A user may place a finger at any point along the bar to position the club at that point in the playback. Dragging a finger along the bar continuously repositions the club to the new playback position, allowing one to animate the club over a specific range at a specific speed.

Figure 7B:
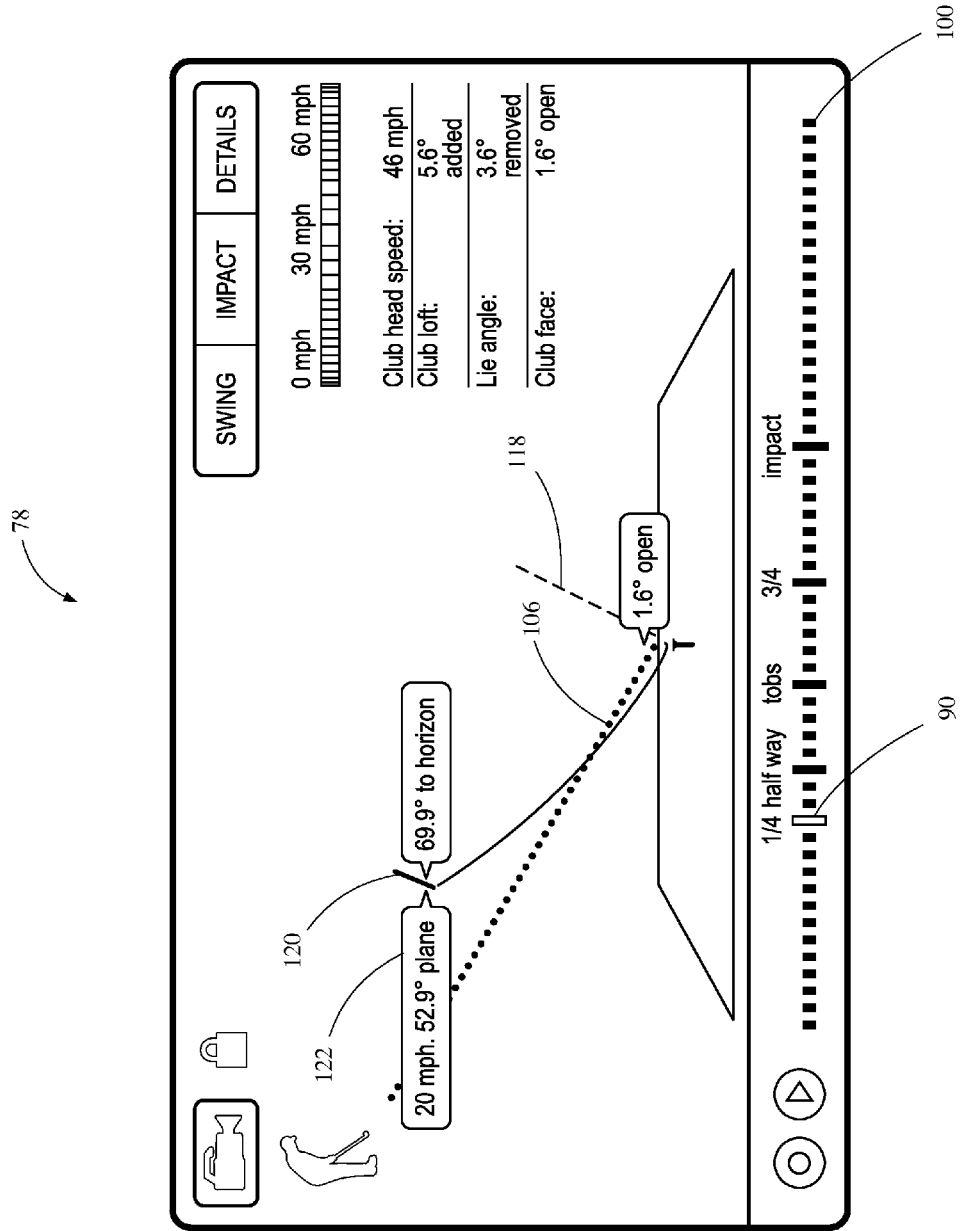
FIG. 7B shows a swing display screen 78 for the application running on a mobile device with statistics at ¼ the way point through a swing.
Figure 7C:
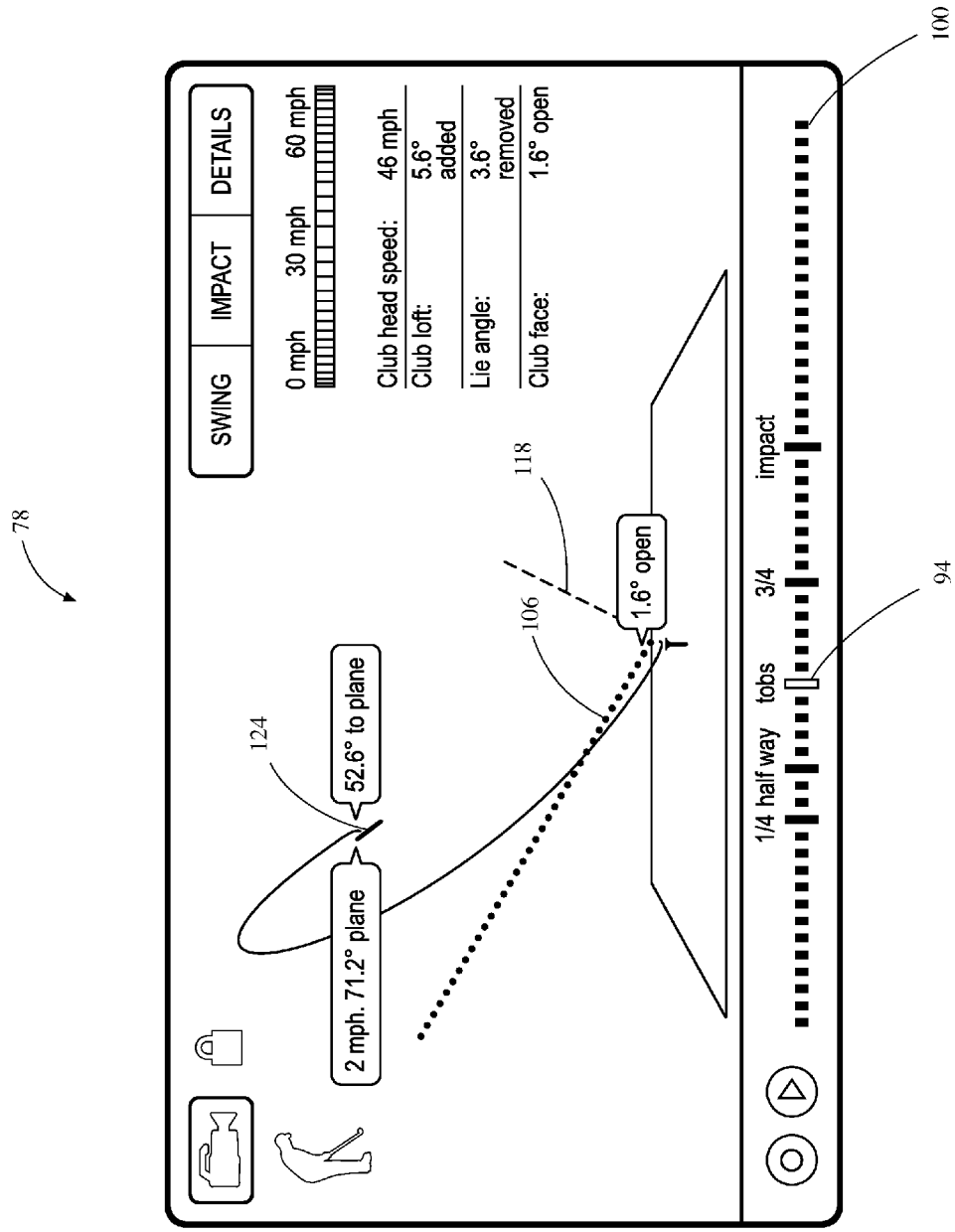
FIG. 7C shows a swing display screen for the application running on a mobile device with statistics at the top of a back swing.
Figure 7D:
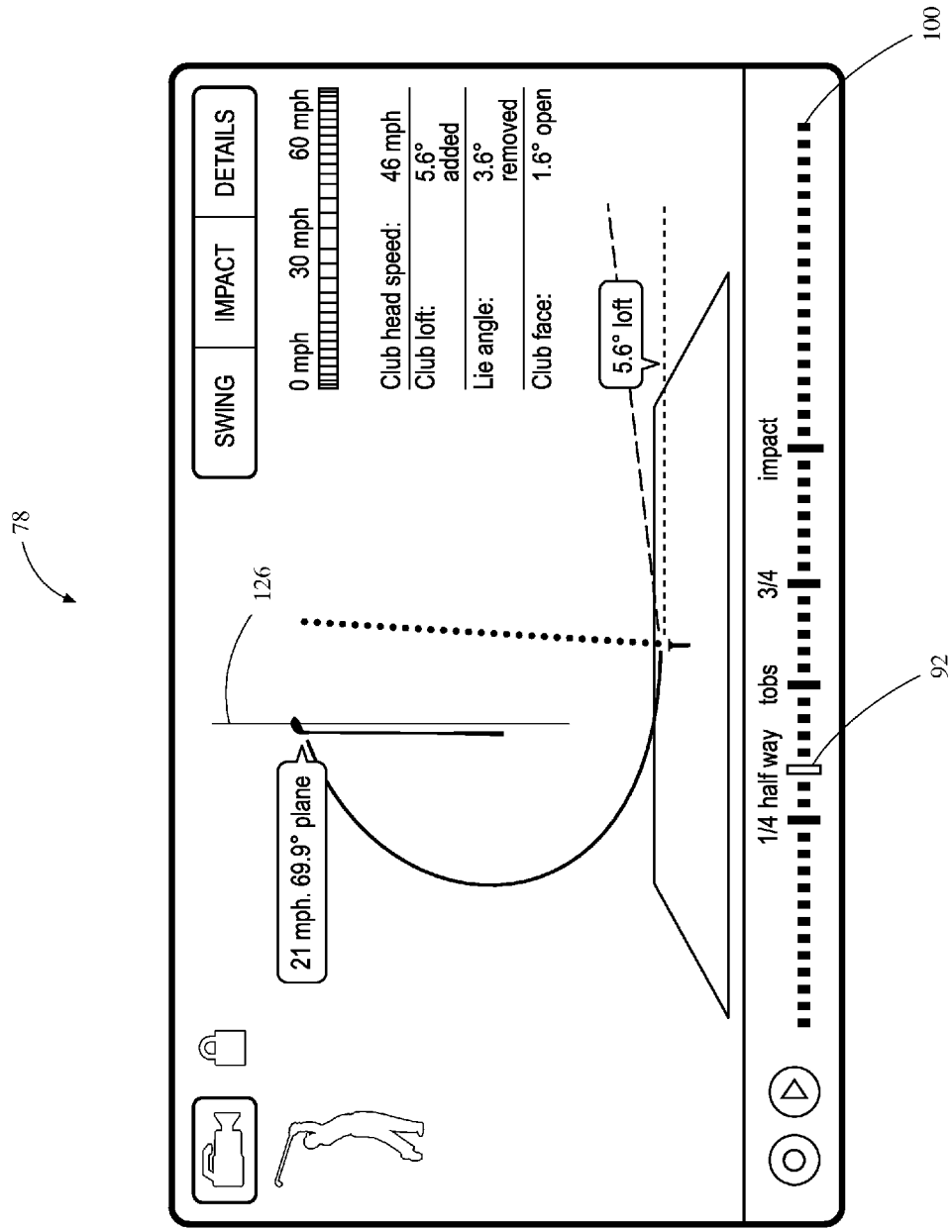
FIG. 7D shows a swing display screen for the application running on a mobile device with statistics at half-way point of a swing.

FIG. 7B shows a swing display screen 78 for the application running on a mobile device with statistics at ¼ the way point through a swing. The club-in-swing position bar 100 is lit up to the ¼ way marker 90. The ball launch direction 118 is shown for comparison along with the angle of the club face to the horizon 120 and other club at point information 122, such as club speed and club plane at a particular point. FIG. 7C shows a swing display screen 78 for the application running on a mobile device with statistics at the top of a back swing. The club-in-swing position bar 100 is lit up to the tobs marker 94. Along with other statistics previously described, the angle of club face to initial plane 124 is shown for comparison with the club initial orientation 106 and the ball launch direction 118. The user may analyze this data and make proper adjustments to improve his or her swing. FIG. 7D shows a swing display screen 78 for the application running on a mobile device with statistics at half-way point of a swing. The club-in-swing position bar 100 is lit up to the half-way marker 92. As with earlier described screens, relevant statistics are shown for comparison and analysis. A user may use a finger or other input device to draw a free-hand line 126 across areas of the swing display screen 78 to mark characteristics of a desired swing and later compare the free-hand line 126 with the actual swing.

Figure 8:
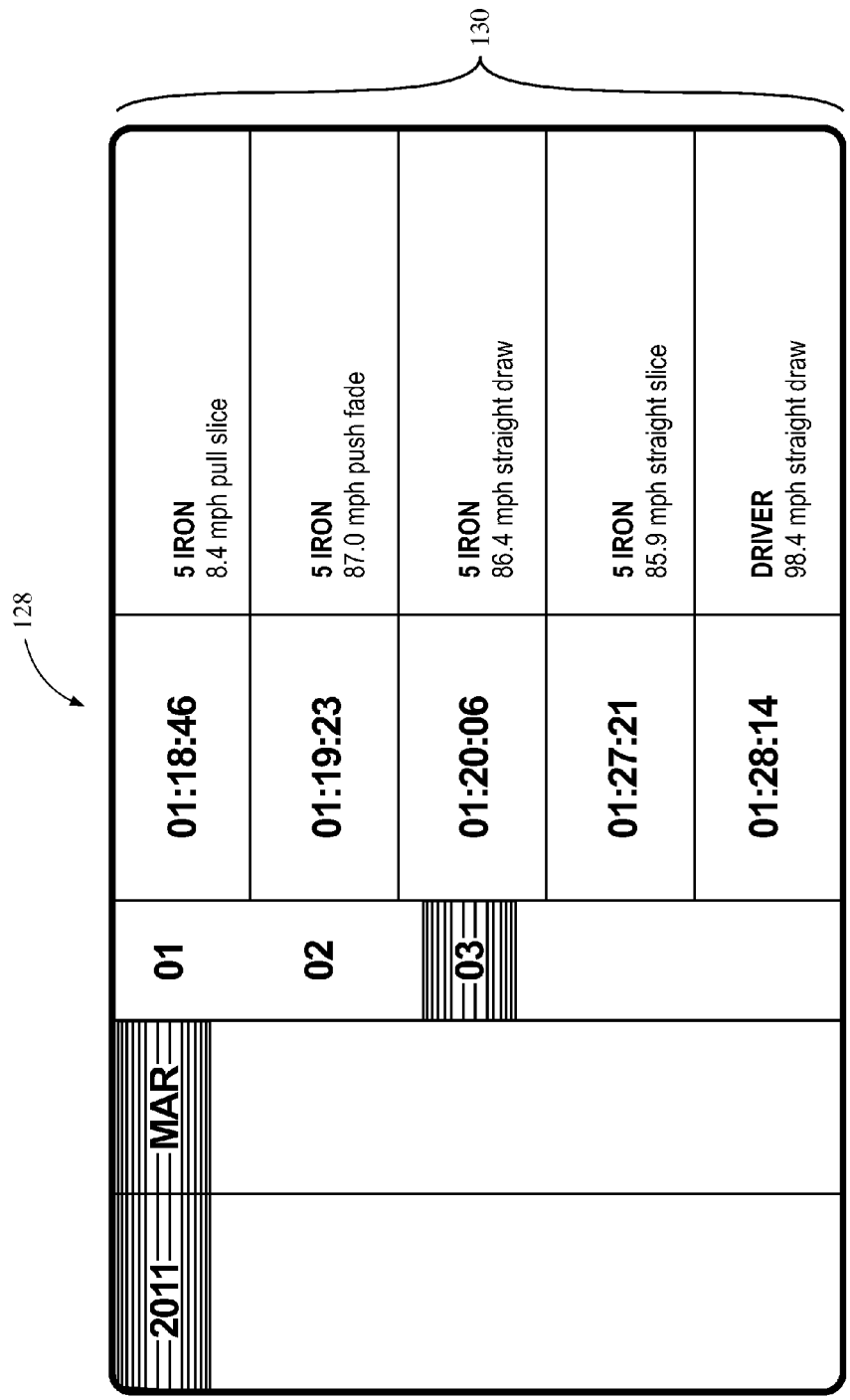
FIG. 8 shows a swing selection screen 128 with a table of swing descriptions for a period of time.

FIG. 8 shows a swing selection screen 128 with a table of swing descriptions for a period of time. The swing selection screen 128 allows a user to view daily swing information 130 by selecting a particular date. The information shown are swing descriptions based on launch angles. Other combinations of data may be displayed.

Figure 9:
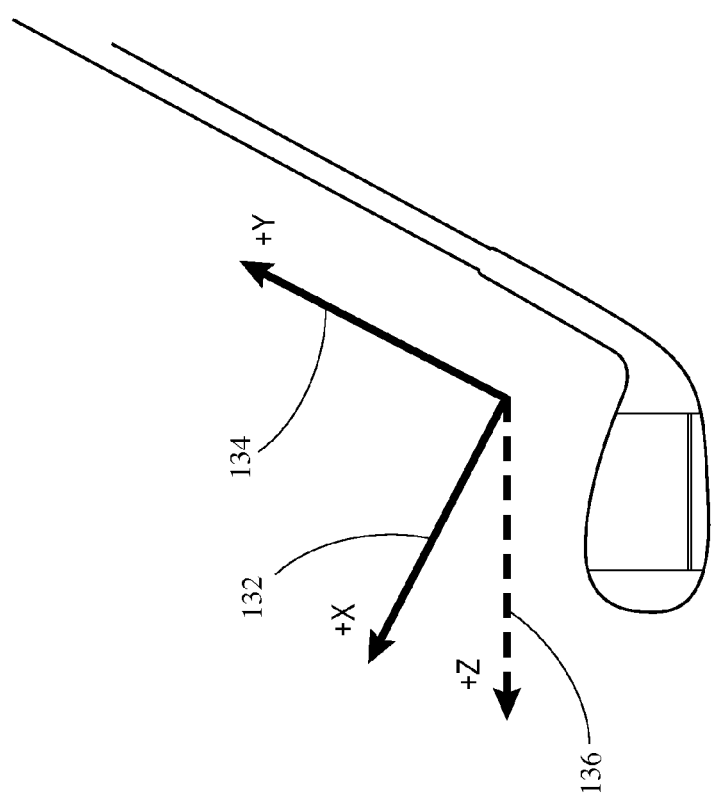
FIG. 9 shows the coordinate system used to describe the algorithm for the principles of operation.

FIG. 9 shows the coordinate system used to describe the algorithm for the following principles of operation. Using the earth as a reference point, the x-axis 132 and the z-axis 136 define the plane along the "ground". The y-axis 134 is straight out of or perpendicular to the "ground". The face-on view is the y-z plane. The down-the-line view is the x-y plane, and the overhead view is the x-z plane.

The following paragraphs describe the algorithm for the principles of operation.

A fixed right-orthogonal coordinate system $0X_g Y_g Z_g$ is selected, located at the starting position of the object. $0Y_g$ is directed at the zenith. Axes $0X_g$ and $0Z_g$ are horizontal, with $0X_g$ having an arbitrary position within the horizontal plane. A right coordinate system is associated with the object, the axes of which coincide with the fixed coordinate system in the initial position. The angular position of the object in the fixed coordinate system is determined by Euler angles $\alpha$, $\beta$ and $\gamma$, with transitions defined from the fixed coordinate system axes.

The relationship between the angular velocities of the object's orientation and angular velocities of the object's rotation in the associated axes is defined by $$\dot{\beta} = \omega_y \sin\gamma + \omega_z \cos\gamma;$$

$$\dot{\alpha} = \frac{1}{\cos\beta}(\omega_y \cos\gamma - \omega_z \sin\gamma);$$

$$\dot{\gamma} = \omega_x - tg\beta(\omega_y \cos\gamma - \omega_z \sin\gamma).$$

Integration of these non-linear equations theoretically allows one to obtain the angles of orientation. However, this is impractical in light of the following calculations, and at the angle $\beta=90°$ ($\cos\beta=0$). In light of this, inertial navigation uses different methods to describe the orientation of the object. Description is most frequently accomplished using direction cosines.

With the unit vectors placed along axes of the fixed and associated coordinate systems with the same identifiers, the transition from the fixed coordinate system to the associated one is defined by the transformation $[x,y,z]^T=P[x_g,y_g,z_g]^T$, where P is a matrix of direction cosines $$P = \begin{vmatrix} P_{11} & P_{12} & P_{13} \\ P_{21} & P_{22} & P_{23} \\ P_{31} & P_{32} & P_{33} \end{vmatrix}$$

The elements of this matrix will then have the following structure:

$P_{11} = \cos\alpha\cos\beta;\quad P_{21} = \sin\alpha\sin\gamma - \cos\alpha\sin\beta\cos\gamma;$ $P_{12} = \sin\beta;\quad P_{22} = \cos\beta\cos\gamma;$ $P_{13} = -\sin\alpha\cos\beta;\quad P_{23} = \cos\alpha\sin\gamma + \cos\gamma\sin\alpha\sin\beta;$ $P_{31} = \cos\gamma\sin\alpha + \sin\beta\sin\gamma\cos\alpha;$ $P_{32} = -\sin\gamma\cos\beta;$ $P_{33} = \cos\alpha\cos\gamma - \sin\alpha\sin\beta\sin\gamma.$ To obtain the current values of the matrix elements, we integrate Poisson's equation $\dot{P}=[\omega]P$, where $[\omega]$, the rotational matrix, is $$[\omega] = \begin{vmatrix} 0 & \omega_z & -\omega_y \\ -\omega_z & 0 & \omega_x \\ \omega_y & -\omega_x & 0 \end{vmatrix}$$

where $\omega_x$, $\omega_y$, $\omega_z$ are angular velocities of the rotation of the object in the associated axes. The matrix elements found through integration are used to compute the current values of the angles of orientation using $$\beta = \mathrm{arc}tgz\frac{P_{12}}{\sqrt{P_{22}^2 + P_{32}^2}};$$

$$\alpha = \mathrm{arc}tgz\frac{-P_{32}}{P_{22}};$$

$$\gamma = \mathrm{arc}tgz\frac{-P_{13}}{P_{11}}.$$

To obtain these formulae, one must use the structure of the matrix of direction cosines. The initial conditions for integrating Poisson's equation are determined during the initialization phase (initial calibration) of the inertial module.

The determination of parameters of the trajectory (linear velocities and coordinates) is done by integrating components of the relative acceleration vector in the fixed coordinate system:

$$[V_x V_y V_z]^T = \int_0^T W_g\, dt + [V_{x0} V_{y0} V_{z0}]^T;$$

$$[x_g y_g z_g]^T = \int_0^T [V_x V_y V_z]^T dt + [x_{g0} y_{g0} z_{g0}]^T.$$

The calculation of the components of the vector of relative acceleration is done according to $W_g=P^T W-[g]$, where W is the vector of apparent acceleration, the components of which are measured by the accelerometers of the inertial module, and [g] is acceleration due to gravity at the point of the current location of the module on the earth's surface, with components $g_x=0$; $g_y=g$; $g_z=0$;

Computing the acceleration due to gravity is done through $g=g_1(1+\beta\sin^2\phi+\beta_1\sin^2 2\phi),$ where $\phi$ is the geographic (geodesic) latitude of the location of the object:

$\beta=0.0053172$; $\beta_1=0.0000071$; $g_1=9,78049$ m/s$^2$

The initialization procedure is done with the module immobilized in the initial position. The goal of the procedure is an estimate of the 0 values and trends of the gyroscopes, and also the elements of the matrix of direction cosines determining the initial orientation of the object. The first problem, the error values of the gyroscopes, is presented as $\Delta\omega=\Delta\omega_0+\chi t+n(t)$, where $\Delta\omega_0$ is the shift of the 0-value, $\chi$ is the speed of the trend, and n(t) is the noise of the sensor. The estimate of parameters $\Delta\omega_0$ and $\chi$ is done through a method of least-squares applied to a recorded set of measurements of gyroscope values during the period of initialization. Three elements of the matrix of direction cosines of the initial orientation of the object are determined by solving the algebraic equation $W=PW'_g$, where $W'_g=[0\ g\ 0]^T$ is the vector of the apparent acceleration of the object in the immobilized system of coordinates during initialization. From this, $$P_{12}(0) = \frac{\overline{W}_x(0)}{g};\ P_{22}(0) = \frac{\overline{W}_y(0)}{g};\ P_{22}(0) = \frac{\overline{W}_z(0)}{g},$$

where $\overline{W}_x(0)$, $\overline{W}_y(0)$, $\overline{W}_z(0)$ are the average values of the apparent accelerations of the object during the period of initialization. The formulae for determining the remaining elements of direction cosines are found from equations determining its structure given that $\alpha=0$.

Some additional considerations are that the system relies heavily on noise filtering algorithms to improve the device's accuracy over time. Additional correction is performed by assuming that the starting point of the club face is at the location of the ball, and that the club passes through that point again on the down-swing. The precise time that the club is passing through this location is determined by locating a shock value in the accelerometer data. The trajectory of the club is then corrected based on this information, reducing the error by more than 50%.

While the present inventions have been illustrated by a description of various embodiments and while these embodiments have been set forth in considerable detail, it is intended that the scope of the inventions be defined by the appended claims. It will be appreciated by those skilled in the art that modifications to the foregoing preferred embodiments may be made in various aspects. It is deemed that the spirit and scope of the inventions encompass such variations to be pre-

What is claimed is:

1. An apparatus for analyzing a golf swing comprising:
a housing for attachment of the apparatus on a golf club;
a power source in the housing;
a three-axis accelerometer in the housing for generating linear acceleration data from the apparatus;
a three-axis gyroscope in the housing for generating angular velocity data from the apparatus;
a first microprocessor in the housing and in communication with the accelerometer and the gyroscope for receiving the linear acceleration data and the angular velocity data;
a first computer memory in the housing and in communication with the first microprocessor;
a radio transmitter, in the housing and in communication with the first microprocessor, that transmits the linear acceleration data and the angular velocity data from the first computer memory;
a portable device comprising:
   a radio receiver, in the portable device and in communication with the radio transmitter, that receives the linear acceleration data and the angular velocity data from the radio transmitter;
   a second computer memory, in the portable device and in communication with the radio receiver, that stores the linear acceleration data and the angular velocity data;
   a third computer memory in the portable device for storing a computer program that processes the data in the second computer memory;
   a second microprocessor, in the portable device and in communication with the second computer memory and the third computer memory, that inputs angular velocity data from the second computer memory, that outputs data representing coordinates estimating the position of the gyroscope corresponding with a 0-error in angular velocity data, that outputs values defining an error trend of the angular velocity data from the gyroscope, and that uses the angular velocity data from the second computer memory to output data representing the initial orientation of the gyroscope;
   said second microprocessor further in communication with said second memory, where said second microprocessor inputs linear acceleration data from the second computer memory, outputs data representing coordinates where the accelerometer produced data that indicates a shock, and controls the computer program to process the linear acceleration data received by the radio receiver into graphical data and statistical data and that transmits the graphical data and statistical data;
   a fourth computer memory in communication with the second microprocessor that receives and stores the graphical data and statistical data; and
   a graphics display that displays the graphical data and statistical data in the fourth memory as an image of the movement of the golf club along with related statistics.

2. The apparatus recited in claim 1 further comprising a three-axis magnetometer capable of transmitting directional orientation data to the first microprocessor.

3. The apparatus recited in claim 1 wherein the portable device is one of a smart phone, a tablet computer, and a portable computer.

4. The apparatus recited in claim 1 wherein the housing attaches to the shaft of a golf club below the grip.

5. The apparatus recited in claim 1 wherein the housing attaches to the shaft of a golf club at the top of the grip.

6. The apparatus recited in claim 1 wherein a hollow golf club shaft is used as the housing.

7. The apparatus recited in claim 1 wherein the graphics display shows an interactive three-dimensional animation of the swing.

8. The apparatus recited in claim 7 wherein the animation can be played as slowly or as quickly as a user desires.

9. The apparatus recited in claim 7 wherein the animation can be played from any angle and at any magnification.

10. The apparatus recited in claim 7 wherein the graphics display can show the position, orientation, and speed of the golf club at any point throughout the swing.

11. The apparatus recited in claim 1 wherein the computer program causes the graphics display to show metrics that allow one to analyze a golf swing including at least one of club head speed at any point in the swing, club and ball path, tempo, top of backswing, angle of attack, relevant planes, and relevant angles.

12. The apparatus recited in claim 1 further comprising a website wherein the second microprocessor controls the computer program in the third computer memory to upload the graphical data and the statistical data from the fourth computer memory to the website for personal review and for sharing with other users.

13. The apparatus recited in claim 12 wherein the website provides coaching based on the linear acceleration data and the angular velocity data.

14. The apparatus recited in claim 12 wherein the website allows a user to compare multiple swings at once using that user's history of uploaded swings, allows a user to enter biometric data and to view baseline swings for that user's body type, and allows a user to see professional and theoretical swings, which allows a user to see trends over time and get objective progress data.

15. The apparatus recited in claim 1 wherein the computer program compares the position of the club when the user aims with the position of the club on impact and calculates the difference in loft, lie and club face angles between the two positions to allow the user to compare what the user meant to do with what actually happened.

16. The apparatus recited in claim 1 further comprising verbal instructions and analysis of the golf club swing.

17. The apparatus recited in claim 1 further comprising:
a user input device for inputting a user's biometric data; and
a fifth computer memory for storing user biometric data;
wherein the second microprocessor controls the computer program to factor the user biometric data into the linear acceleration data and the angular velocity data.

18. The apparatus recited in claim 1 wherein the housing is of a weight light enough to not affect a user's swing.

19. An apparatus for analyzing a golf swing comprising:
a golf club;
a housing attachable to the golf club;
a power source in the housing;
a motion detector coupled to the golf club comprising:
   a three-axis MEMS accelerometer in the housing for generating linear acceleration data from the apparatus;
   a three-axis MEMS gyroscope in the housing for generating angular velocity data from the apparatus;
   a three-axis magnetometer in the housing for generating directional orientation data from the apparatus;

a first microprocessor in the housing and in communication with the accelerometer, the gyroscope and the magnetometer for receiving the linear acceleration data, the angular velocity data and the directional orientation data;

a first computer memory in the housing and in communication with the first microprocessor; and a radio transmitter in the housing and in communication with the first microprocessor that transmits the linear acceleration data, the angular velocity data and the directional orientation data from the first computer memory;

a portable device comprising:

a radio receiver in the portable device and in communication with the radio transmitter, that receives the linear acceleration data, the angular velocity data and the directional orientation data from the radio transmitter;

a second computer memory in the portable device and in communication with the radio receiver that stores the linear acceleration data, the angular velocity data and the directional orientation data;

a third computer memory in the portable device for storing a computer program that processes the data in the second computer memory;

a second microprocessor in the portable device and in communication with the second computer memory and the third computer memory that inputs angular velocity data from the second computer memory, that outputs data representing coordinates estimating the position of the gyroscope corresponding with a 0-error in angular velocity data, that outputs values defining an error trend of the angular velocity data from the gyroscope, and that uses the angular velocity data from the second computer memory to output data representing the initial orientation of the gyroscope;

said second microprocessor further in communication with said second memory, where said second microprocessor inputs linear acceleration data from the second computer memory, outputs data representing coordinates where the accelerometer produced data that indicates a shock, and controls the computer program to process the linear acceleration data received by the radio receiver into graphical data and statistical data and that transmits the graphical data and statistical data;

said second microprocessor further in communication with said second memory, where said second microprocessor inputs directional orientation data from the second computer memory and uses the directional orientation data to output data to select the target line on which a golfer wishes to aim;

a fourth computer memory for receiving graphical data and statistical data from the second microprocessor; and a graphics display that displays the graphical data and statistical data in the fourth memory as an image of the movement of the golf club along with related statistics.

20. A method for analyzing a golf swing comprising:
providing a golf club;
attaching a housing to the golf club;
inserting a power source in the housing;
providing a motion detector coupled to the golf club comprising:
generating linear acceleration data from the apparatus using a three-axis MEMS accelerometer in the housing;
generating angular velocity data from the apparatus using a three-axis MEMS gyroscope in the housing;
generating directional orientation data from the apparatus using a three-axis magnetometer in the housing;
providing a first microprocessor in the housing and in communication with the accelerometer, the gyroscope and the magnetometer and receiving the linear acceleration data, the angular velocity data and the directional orientation data;
providing a first computer memory in the housing and in communication with the first microprocessor; and
transmitting the linear acceleration data, the angular velocity data and the directional orientation data from the first computer memory using a radio transmitter in the housing; and
providing a portable device comprising:
receiving the linear acceleration data, the angular velocity data and the directional orientation data from the radio transmitter using a radio receiver in the portable device;
storing the linear acceleration data, the angular velocity data and the directional orientation data in a second computer memory in the portable device;
storing a computer program in a third computer memory in the portable device that processes the data in the second computer memory;
providing a second microprocessor in the portable device and in communication with the second computer memory and the third computer memory that inputs angular velocity data from the second computer memory, that outputs data representing coordinates estimating the position of the gyroscope corresponding with a O-error in angular velocity data, that outputs values defining an error trend of the angular velocity data from the gyroscope, and that uses the angular velocity data from the second computer memory to output data representing the initial orientation of the gyroscope;
further providing said second microprocessor in communication with said second memory, where said second microprocessor inputs linear acceleration data from the second computer memory, outputs data representing coordinates where the accelerometer produced data that indicates a shock, and controls the computer program to process the linear acceleration data received by the radio receiver into graphical data and statistical data and that transmits the graphical data and statistical data;
further providing said second microprocessor in communication with said second memory, where said second microprocessor inputs directional orientation data from the second computer memory and uses the directional orientation data to output data to select the target line on which a golfer wishes to aim;
receiving graphical data and statistical data from the second microprocessor into a fourth computer memory; and
displaying an image of a golf club swing and statistical data on a graphics display.

* * * * *